(12) United States Patent
Kumar et al.

(10) Patent No.: US 6,957,959 B2
(45) Date of Patent: Oct. 25, 2005

(54) DENTAL HAND TOOL WITH RATCHET MECHANISM

(75) Inventors: Ajay Kumar, Palmdale, CA (US); Ines Aravena, Camarillo, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 97 days.

(21) Appl. No.: 10/302,127

(22) Filed: Nov. 22, 2002

(65) Prior Publication Data

US 2003/0224322 A1     Dec. 4, 2003

Related U.S. Application Data

(60) Provisional application No. 60/385,544, filed on Jun. 4, 2002.

(51) Int. Cl.⁷ .............................. A61C 3/00; B25B 13/46
(52) U.S. Cl. ............................................. 433/141; 81/60
(58) Field of Search ................................. 433/141, 146, 433/147; 81/60, 58.4, 58.2, 480, 489, 63.1

(56) References Cited

U.S. PATENT DOCUMENTS

| | | | | |
|---|---|---|---|---|
| 4,474,089 A | * | 10/1984 | Scott ......................... | 81/57.29 |
| 5,685,204 A | * | 11/1997 | Braun ........................ | 81/63.1 |
| 5,836,430 A | * | 11/1998 | Vasudeva ................... | 192/43.2 |
| 2002/0002881 A1 | * | 1/2002 | Glass ......................... | 81/58.3 |

* cited by examiner

*Primary Examiner*—Cary E. O'Connor
(74) *Attorney, Agent, or Firm*—Conley Rose, P.C.

(57) ABSTRACT

A manual dental driving tool adapted to drive a dental implant into the jawbone of a patient. The driving tool includes a handle at the proximal end, a ratchet assembly and a pin assembly located within the handle, and a tool engaging assembly located at the distal end. The pin assembly switches the driving tool between a manual mode and a ratchet mode.

31 Claims, 3 Drawing Sheets

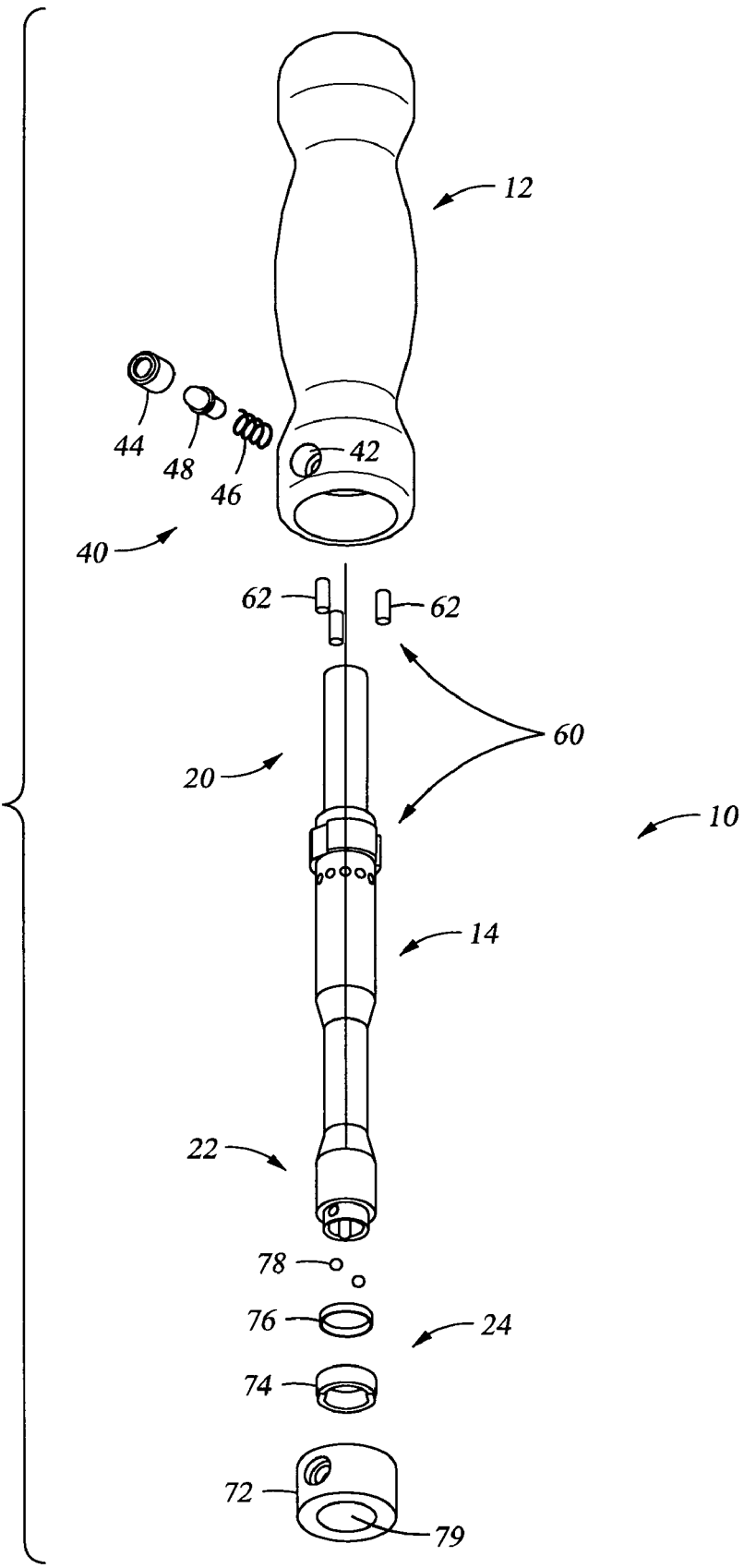

DENTAL HAND TOOL WITH RATCHET MECHANISM

CROSS-REFERENCE TO RELATED APPLICATIONS

This application claims benefit of priority of U.S. Provisional Application Ser. No. 60/385,544 filed Jun. 4, 2002.

FIELD OF THE INVENTION

The present invention relates generally to the field of dental implantology and, more specifically, to a dental hand tool for carrying and then manually driving a dental implant in a prepared surgical site in a jawbone of a patient.

BACKGROUND OF THE INVENTION

In order to install a threaded dental implant into the jawbone of a patient, the gingival tissue is incised and the jawbone is exposed. A series of drills are then used to form a cylindrical bore (referred as the osteotomy) in the bone. Once the osteotomy is prepared, the distal end of the implant is positioned in the bore, and a driving tool is used to rotate and drive the implant into the osteotomy.

In some instances, a fixture mount is attached to the top of the implant with a retaining screw. The fixture mount serves as an intermediate member between the implant and driving tool. The driving tool directly engages the fixture mount and imparts torque to it to drive the implant. When no fixture mount is used, a distal end of the driving tool directly engages the coronal end of the implant.

During the implantation procedure, a manual or hand-held driving tool can be used to drive the dental implant into the osteotomy. Typically, such driving tools include a proximal end with a hand-grip and a long shaft that has a distal end for driving the implant. Often, the distal end connects to a dental driver that, in turn, directly connects to the implant or fixture mount. This distal end may have, for example, a square geometry with a retention feature that engages and holds the dental driver.

Conventional manual driving tools have many disadvantages. In order to drive the implant into the jawbone, the surgeon must repeatedly turn or twist the end of the driving tool. Many hand and wrist rotations may be required to fully seat a threaded implant into the osteotomy. Surgeons are prone to get carpal tunnel syndrome from this repeated, twisting motion.

Threaded dental implants need to be placed into the osteotomy with precision. In this regard, unnecessary lateral movement of the implant should be avoided as the implant is driven into the bone. Lateral movement, especially in soft or cancellous bone, can disrupt proper placement of the implant and hinder osseointegration with surrounding bone and tissue.

Conventional manual dental driving tools are also prone to impart unnecessary lateral movement to implants during placement. Specifically, in order to rotate and drive the implant, the surgeon must repeatedly grip and re-grip the end of driving tool handle. While the handle is being gripped and re-gripped, the surgeon forgoes some control of the handle. In these instances, the handle can slip or otherwise accidentally move in the surgeon's hand. Unnecessary movement of the handle can impart large, unwanted movements to the implant since the implant is connected to the handle via a long fulcrum or arm.

It would be advantageous to have a dental driving tool that could be used to manually drive the implant into the osteotomy but did not have the disadvantages of prior devices.

BRIEF SUMMARY OF PREFERRED EMBODIMENTS OF THE INVENTION

The present invention is directed toward a manual dental driving tool adapted to drive a dental implant into the jawbone of a patient. The driving tool includes a handle at the proximal end, a ratchet assembly and a pin assembly located within the handle, and a tool engaging assembly located at the distal end.

One advantage of the present invention is that the ratchet assembly can be used to rotate the drive shaft of the driving tool and drive the dental implant into the osteotomy. The ratchet assembly reduces the extent or degree of hand and wrist rotations to drive the implant and, thus, reduces the likelihood of carpal tunnel syndrome.

Another advantage of the present invention is that the surgeon is not required to grip and re-grip the handle in order to drive the implant with the driving tool. The ratchet assembly grips and re-grips the drive shaft while the surgeon's hands remain on the handle. As such, the likelihood that the handle slips or accidentally moves is reduced.

An important advantage of the present invention is the function and use of the pin assembly. This assembly enables the surgeon to switch the driving tool between two modes of use: A ratchet mode and a manual mode. In the ratchet mode, the ratchet assembly engages the drive shaft and drives the implant. In the manual mode, the ratchet assembly is disengaged, and manual rotation of the handle rotates the drive shaft and drives the implant.

In the manual mode, the implant can be manually rotated in fine, discrete increments. Such rotation enables fine adjustments and more exact placement of the implant. Further, the manual mode provides consistent tactile feedback while the implant is being driven, especially when the implant is placed in soft, cortical bone.

Accordingly, the present invention comprises a combination of features and advantages that overcome various problems, deficiencies, or shortcomings associated with prior devices. The various features and advantages of the invention will be readily apparent to those skilled in the art upon referring to the accompanying drawings and reading the following detailed description of the preferred embodiments of the invention.

BRIEF DESCRIPTION OF THE DRAWINGS

For a more detailed description of preferred embodiments of the present invention, reference will now be made to the accompanying drawings, wherein:

FIG. 2 is an exploded view of an unassembled dental driving tool shown in FIG. 1.

DETAILED DESCRIPTION OF PREFERRED EMBODIMENTS

Figure 1:
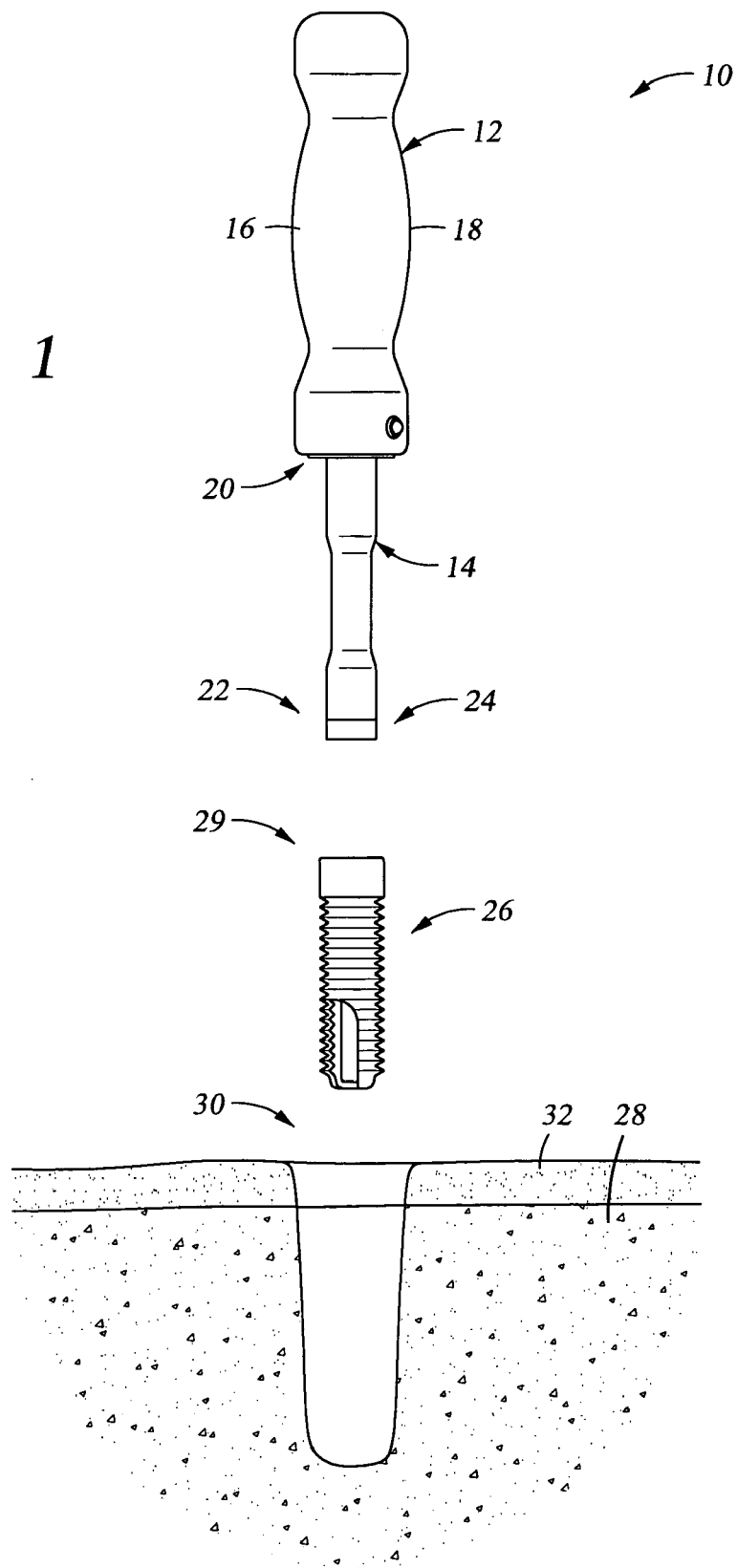
FIG. 1 is a solid view of an assembled dental driving tool, a dental implant, and a prepared osteotomey of a patient in accordance with a preferred embodiment of the present invention.

FIG. 1 shows the dental driving tool 10 of the present invention. The driving tool generally has an elongated body with a handle 12 and drive shaft 14. The handle has an exterior surface 16 with a hand-grip portion 18 adapted to receive a hand for manual rotation. A proximal end 20 of drive shaft 14 connects to handle 12. A distal end 22 of the drive shaft includes a tool engaging assembly 24 adapted to engage and drive a threaded dental implant 26 into a jawbone 28 of a human patient.

As shown in FIG. 1, implant 26 is positioned above an osteotomy 30. A cylindrical bore is formed in the gingival tissue 32 and jawbone 28, and the osteotomy is ready to receive the implant. Once the driving tool engages the implant and the distal end of the implant is positioned in the osteotomy 30, the driving tool 10 is rotated and the implant is driven into the bone. Specifically, when the handle 12 is manually rotated, torque transfers from the handle and to the drive shaft 14. The distal end 22 of the drive shaft transfers torque to a coronal end 29 of the implant.

The implant 26 may be any one of various implants known to those skilled in the art, such as a straight Screw-Vent implant of Centerpulse Dental Inc., and may be placed in the jawbone according to techniques known to those skilled in the art. Preferably, the implant 26 is made of titanium or another strong and biocompatible metal and includes a generally cylindrical body having external threads and coronal end 29 for engaging the distal end 22 of the driving tool. Coronal end 29 of the implant includes an engaging feature adapted to engage the distal end of the driving tool. This engaging feature can be various configurations known to those skilled in the art, such as splines, external or internal hexagon, octagon, star, polygons, or other geometries or retention mechanisms.

FIG. 2 shows the driving tool 10 in more detail. A pin assembly 40 is located in the handle 12 and generally functions to switch the driving tool between two different modes of operation: A manual mode and a ratchet mode. The pin assembly is located in a bore 42 through the distal end of the handle. The assembly generally includes a housing 44, a biasing member 46, and a locking member 48, such as a button, a pin, a cylinder, or the like. The housing press-fits into the bore 42 and holds the button and biasing member. The biasing member 46 is preferably a spring and biases the button 48 upwardly and away from the drive shaft 14 and handle 12.

The proximal end 20 of drive shaft 14 includes a ratchet assembly 60. This assembly 60 includes at least one roller member 62 and a bearing surface or inner race 64. Here, the roller member 62 is shown as three elongated, cylindrical rollers, but other devices known to those skilled in the art (such as bearings or ball bearings) may be used as well.

Figure 4:
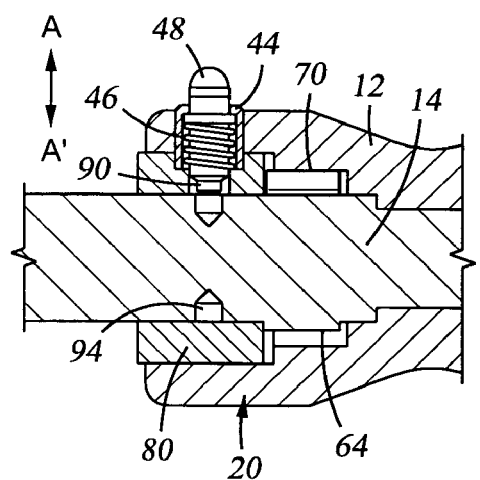
FIG. 4 is a cross-sectional view of the pin assembly and ratchet assembly.
Figure 5:
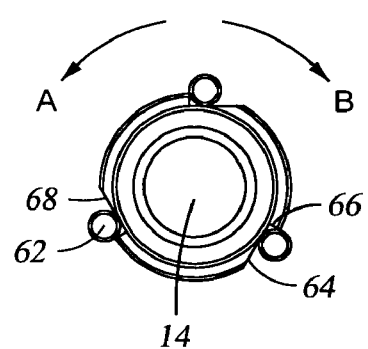
FIG. 5 is an end view of the ratchet assembly.

The ratchet assembly 60 works in a manner known to those skilled in the art. As shown in FIGS. 4 and 5, the inner race 64 is formed on an outer surface of drive shaft 14. When handle 12 is rotated in a counterclockwise direction, shown as arrow A, the roller members 62 abut against a wall 66 and are disengaged or out of engagement. In this instance, the handle 12 freely rotates, and the drive shaft 14 does not rotate when the handle is turned. When the handle is rotated in a clockwise direction, shown as arrow B, the roller members move up surface 68 and become jammed or wedged between surface 68 and outer race 70. In this instance, the roller members are engaged between two surfaces and, thus, torque from the handle is transferred to the drive shaft. Here, the handle and drive shaft rotate together.

Turning back to FIG. 2, the distal end 22 of the drive shaft 14 includes the tool engaging assembly 24. This assembly may have various configurations. It may, for example, be configured to connect directly to a proximal or coronal end of a dental implant or a fixture mount. Alternatively, it may be configured to connect to a dental driver, such as hexagonal driver (not shown). The tool engaging assembly, thus, can be configured to connect to splines, external or internal hexagons, octagons, stars, squares, polygons, or other geometries or retention mechanisms.

In FIG. 2, the tool engaging assembly 24 is configured to receive, engage, carry, and drive a separate dental driver (not shown). The assembly generally uses a spring-biased, ball-detent mechanism. The assembly includes a housing 72, a locking mechanism 74, a ring-spring 76, and two bearings 78 that all fit into the housing. Once assembled, the bearings partially protrude into an opening 79 formed in the housing 72. This opening receives an end of the dental driver (not shown), and the bearings 78 frictionally engage this end to hold the dental driver.

Figure 3A:
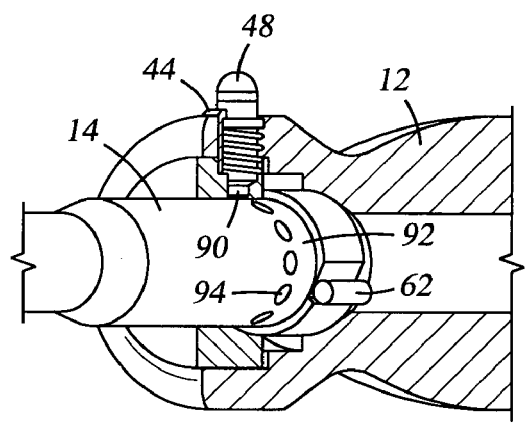
FIG. 3A is a first enlarged, partial perspective view of the pin assembly and ratchet assembly of the dental driving tool of FIG. 1.
Figure 3B:
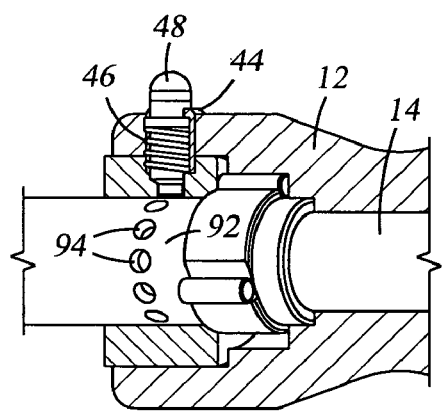
FIG. 3B is a second enlarged, partial perspective view of the pin assembly and ratchet assembly of the dental driving tool of FIG. 1.

Looking now to FIGS. 3A, 3B, and 4, one important advantage of the present invention is the function and use of the pin assembly 40 and ratchet assembly 60. The pin assembly enables the surgeon or user to switch the driving tool 10 between two different modes of use: A ratchet mode and a manual mode. In the ratchet mode, the ratchet assembly is used to rotate and drive the implant. In the manual mode, the ratchet assembly is disengaged, and manual rotation of the handle 12 rotates the drive shaft and drives the implant.

As shown best in the FIGS. 3A, 3B, and 4, a locking ring 80 holds the proximal end 20 of the drive shaft 14 into the distal end of the handle 12. Further, the button 48 is moveable in a radial direction (shown along arrows A and A') that is perpendicular to the drive shaft 14. The button slides up and down in housing 44 and, preferably, is biased in the upward position. As such, the button has two primary positions: (1) an upward or unlocked position, or (2) a downward or locked position. Preferably, the button is located adjacent the distal end of the handle 12. In this position, the user or surgeon can easily activate or move the button with a thumb or finger without disrupting the grip on the handle.

In the unlocked position, the driving tool is in the ratchet mode. Here, as discussed in connection with FIG. 5, when the handle 12 is rotated in a counterclockwise direction, the handle 12 freely rotates, and the drive shaft 14 does not rotate. When the handle is rotated in a clockwise direction, the roller members are engaged between two surfaces and, thus, torque from the handle is transferred to the drive shaft. Here, the handle and drive shaft rotate together.

The ratchet mode is advantageous since the user or surgeon is not required to grip and re-grip the handle in order to drive the implant with the driving tool. The hand of the surgeon remains on the handle. As such, the likelihood that the handle will slip or that accidental or unwanted movement will occur is reduced.

In the locked position, the driving tool is in the manual mode. Here, the distal end 90 of the button 48 engages a locking mechanism 92. Preferably, the locking mechanism is formed adjacent the proximal end 20 of the drive shaft 14 and includes a plurality of locking members 94. These locking members are preferably formed as indentations. The indentations can have various configurations, such as, partial spheres, squares, grooves, channels, or polygonal formations. Preferably, the distal end of the button has a configuration adapted to mate or lock with the locking mechanism. This locking arrangement between the button and locking mechanism enables the handle to transfer torque to the drive shaft as the handle is rotated in a clockwise or counterclockwise direction. As shown, the distal end 90 protrudes from the button and has a cylindrical shape with a spherical end adapted to fit inside the indentations. It will be appreciated, then, that the configurations of the distal end 90 of the button 48 and the locking mechanism 92 may have various configurations known to those skilled in the art.

In the locked position then, the button engages or locks with the locking mechanism. Here, when the handle is rotated in either the clockwise or counterclockwise direction torque from the handle is transferred to the drive shaft. Thus, in the manual mode, the handle and drive shaft rotate together in both rotational directions.

In the manual mode, the implant can be manually rotated in fine, discrete increments. Such rotation enables fine adjustments and more exact placement of the implant. Further, the manual mode provides consistent tactile feedback while the implant is being driven, especially when the implant is placed in soft, cortical bone, such as the posterior maxilla.

The driving tool 10 may be formed from various materials applicable to the field of dental implantology and known to those skilled in the art. Preferably, the handle is formed from a strong polymer or metal, and the drive shaft is formed from a metal, such as titanium or steel. Further, the biasing member 46 may be formed from a biocompatible, corrosive resistant material, such as titanium.

The present invention can be used with various dental tools, dental implants, and dental accessories, such as an abutment, fixture mount, or other driving apparatus. Further, as understood by those skilled in the art, the precise configuration and dimensions of the various components of driving tool may vary depending upon the size of the implant or device to be installed or other tool to be engaged. The principles of the present invention can be applied to these various components. Further yet, while preferred embodiments of this invention have been shown and described, modifications thereof can be made by one skilled in the art without departing from the spirit or teaching of this invention. The embodiments described herein are exemplary only and are not limiting. Many variations and modifications of the system, apparatus, and methods are possible and are within the scope of the inventions claimed below. Accordingly, the scope of protection is not limited to the embodiments described herein, but is only limited by the claims that follow, the scope of which shall include all equivalents of the subject matter of the claims.

What is claimed is:

1. A dental driving tool, comprising:
    a handle having a hand-grip portion on an exterior surface;
    a drive shaft having a distal end with a tool engaging assembly adapted to engage a dental driver and having a proximal end connected to the handle;
    a first plurality of recesses in said drive shaft;
    a second plurality of recesses in said drive shaft;
    a ratchet assembly located in the handle;
    a pin assembly located in the handle;
    the dental driving tool being operable in two different modes, a ratchet mode and a manual mode, to drive a dental implant into a jawbone of a patient; and
    wherein the ratchet mode uses the ratchet assembly to engage at least one of the first plurality of recesses and drive the dental implant, and the manual mode uses the pin assembly to engage at least one of the second plurality of recesses and drive the dental implant.

2. The dental driving tool of claim 1 wherein the pin assembly includes a biasing member and a pin.

3. The dental driving tool of claim 2 wherein the biasing member biases the pin out of engagement with the at least one of the second plurality of recesses.

4. The dental driving tool of claim 2 wherein the pin engages the at least one of the second plurality of recesses.

5. The dental driving tool of claim 2 wherein the pin assembly further includes a housing; the biasing member and pin located in the housing; and the pin being moveable in the housing to two different positions, one position being the ratchet mode and a second position being the manual mode.

6. The dental driving tool of claim 5 wherein the second plurality of recesses are spherical indentations; and the pin has a spherical end adapted to engage the spherical indentations.

7. A dental driving tool, comprising:
    a handle adapted to be manually rotated;
    a drive shaft having a locking mechanism, a distal end adapted to drive a dental implant into a jawbone, and a proximal end connected to the handle;
    a ratchet assembly at the proximal end of the drive shaft, wherein said ratchet assembly is operated independently from said locking mechanism; and
    a pin assembly at the handle and releasably engageable with the locking mechanism to provide two different modes of drive rotation, a ratchet mode and a manual mode, to drive the dental implant into the jawbone.

8. The dental driving tool of claim 7 wherein the ratchet mode uses the ratchet assembly to drive the dental implant, and the manual mode uses the pin assembly to drive the dental implant.

9. The dental driving tool of claim 8 wherein the pin assembly engages the locking mechanism in the manual mode, and the pin assembly disengages the locking mechanism in the ratchet mode.

10. The dental driving tool of claim 9 wherein the pin assembly includes a spring and a pin, the pin engaging the locking mechanism in the manual mode.

11. The dental driving tool of claim 10 wherein the spring biases the pin to disengage the locking mechanism in the ratchet mode.

12. The dental driving tool of claim 7 wherein the ratchet assembly includes an inner and outer race and at least one roller member disposed between the inner and outer race; the pin assembly includes a biasing member and a button, the button being moveable to actuate the ratchet and manual modes.

13. The dental driving tool of claim 12 wherein the locking mechanism includes indentations adapted to engage the pin assembly in the manual mode.

14. The dental driving tool of claim 13 wherein the indentations are configured as one of partial spheres, grooves, channels, or polygonal recess.

15. A dental driving tool, comprising:
    a handle adapted to be manually rotated;

a drive shaft having a distal end adapted to drive a dental implant into a jawbone and having a proximal end connected to the handle;
a ratchet assembly at the drive shaft and including a race and a roller member;
a pin assembly at the handle and releasably engageable with the drive shaft to provide two different modes of drive rotation, a ratchet mode and a manual mode;
the ratchet mode is adapted to use the ratchet assembly to drive the dental implant into the jawbone; and
the manual mode is adapted to use engagement between the pin assembly and drive shaft to drive the dental implant into the jawbone.

16. The dental driving tool of claim 15 in which the pin assembly locks with the drive shaft in the manual mode so the drive shaft moves in unison when the handle is rotated in a clockwise and counterclockwise direction.

17. The dental driving tool of claim 16 in which the pin assembly is disengaged from the drive shaft in the ratchet mode so the drive shaft moves in unison when the handle is rotated in the clockwise direction.

18. The dental driving tool of claim 17 in which the drive shaft has an elongated configuration and is formed from metal; and the handle has an exterior surface adapted to be hand-gripped and is formed from a polymer.

19. The dental driving tool of claim 17 in which the drive shaft includes a plurality of locking members; and the pin assembly is moveable to engage at least one of the locking members.

20. The dental driving tool of claim 19 in which the ratchet assembly is disengaged while the pin assembly is engaged with the at least one of the locking members.

21. A dental driving tool, comprising:
a handle having a hand-grip portion on a exterior surface;
a drive shaft having a distal end with a tool engaging assembly adapted to engage a dental driver and having a proximal end connected to the handle;
a ratchet assembly located in the handle;
a pin assembly located in the handle;
the dental driving tool being operable in two different modes, a ratchet mode and a manual mode, to drive a dental implant into a jawbone of a patient;
wherein the ratchet mode uses the ratchet assembly to drive the dental implant, and the manual mode uses the pin assembly to drive the dental implant;
wherein the drive shaft includes a locking mechanism; the pin assembly includes a biasing member and a pin; and the pin being moveable to engage the locking mechanism;
wherein the pin engages the locking mechanism to operate the dental driving tool in the manual mode;
wherein the locking mechanism includes a plurality of recesses; and the pin is moveable to engage one of the recesses;
wherein the pin assembly further includes a housing; the biasing member and pin located in the housing; and the pin being moveable in the housing to two different positions, one position being the ratchet mode and a second position being the manual mode; and
wherein the recesses of the locking mechanism are spherical indentations; and the pin has a spherical end adapted to engage the spherical indentations.

22. A dental driving tool, comprising:
a handle adapted to be manually rotated;
a drive shaft having a locking mechanism; a distal end adapted to drive a dental implant into a jawbone, and a proximal end connected to the handle;
a ratchet assembly at the proximal end of the drive shaft;
a pin assembly at the handle and releasably engageable with the locking mechanism to provide two different modes of drive rotation, a ratchet mode and a manual mode, to drive the dental implant into the jawbone;
wherein the ratchet mode uses the ratchet assembly to drive the dental implant, and the manual mode uses the pin assembly to drive the dental implant; and
wherein the pin assembly engages the locking mechanism in the manual mode, and the pin assembly disengages the locking mechanism in the ratchet mode.

23. The dental driving tool of claim 22 wherein the pin assembly includes a spring and a pin, the pin engaging the locking mechanism in the manual mode.

24. The dental driving tool of claim 23 wherein the spring biases the pin to disengage the locking mechanism in the ratchet mode.

25. The dental driving tool of claim 24 wherein the ratchet assembly includes an inner and outer race and at least one roller member disposed between the inner and outer race; the pin assembly includes a biasing member and a button, the button being moveable to actuate the ratchet and manual modes.

26. The dental driving tool of claim 25 wherein the locking mechanism includes indentations adapted to engage the pin assembly in the manual mode.

27. The dental driving tool of claim 26 wherein the indentations are configured as one of partial spheres, grooves, channels, or polygonal recess.

28. A dental driving tool, comprising:
a handle adapted to be manually rotated;
a drive shaft having a distal end adapted to drive a dental implant into a jawbone and having a proximal end connected to the handle;
a ratchet assembly at the drive shaft and including a race and a roller member;
a pin assembly at the handle and releasably engageable with the drive shaft to provide two different modes of drive rotation, a ratchet mode and a manual mode;
the ratchet mode is adapted to use the ratchet assembly to drive the dental implant into the jawbone;
the manual mode is adapted to use engagement between the pin assembly and drive shaft to drive the dental implant into the jawbone;
wherein the pin assembly locks with the drive shaft in the manual mode so the drive shaft moves in unison when the handle is rotated in a clockwise and counterclockwise direction; and
wherein the pin assembly is disengaged from the drive shaft in the ratchet mode so the drive shaft moves in unison when the handle is rotated in the clockwise direction.

29. The dental driving tool of claim 28 in which the drive shaft has an elongated configuration and is formed from metal; and the handle has an exterior surface adapted to be hand-gripped and is formed from a polymer.

30. The dental driving tool of claim 29 in which the drive shaft includes a plurality of locking members; and the pin assembly is moveable to engage at least one of the locking members.

31. The dental driving tool of claim 30 in which the ratchet assembly is disengaged while the pin assembly is engaged with the at least one of the locking members.

* * * * *